United States Patent [19]

Ogura

[11] Patent Number: 4,823,169

[45] Date of Patent: Apr. 18, 1989

[54] REFLECTION DENSITY MEASURING SYSTEM

[75] Inventor: Nobuhiko Ogura, Kanagawa, Japan

[73] Assignee: Fuji Photo Film Co., Ltd., Kanagawa, Japan

[21] Appl. No.: 19,402

[22] Filed: Feb. 26, 1987

[30] Foreign Application Priority Data

Feb. 26, 1986 [JP] Japan ................................ 61-40890
Apr. 19, 1986 [JP] Japan ................................ 61-90956

[51] Int. Cl.$^4$ ........................................... G01N 21/47
[52] U.S. Cl. ..................................... 356/446; 356/430
[58] Field of Search ............... 356/445, 446, 447, 448, 356/430, 431

[56] References Cited

U.S. PATENT DOCUMENTS

| | | | |
|---|---|---|---|
| 3,578,977 | 5/1971 | Natelson ................... | 356/430 |
| 4,037,970 | 7/1977 | Webster et al. ............. | 356/446 |
| 4,252,443 | 2/1981 | Lucas et al. ............... | 356/446 |
| 4,568,191 | 2/1986 | Barry ....................... | 356/446 |
| 4,616,933 | 10/1986 | Leveque et al. ............ | 356/445 |

FOREIGN PATENT DOCUMENTS 61-17046 1/1986 Japan.

Primary Examiner—Richard A. Rosenberger
Attorney, Agent, or Firm—Sughrue, Mion, Zinn, Macpeak and Seas

[57] ABSTRACT

A reflection density measuring system comprises a light source for projecting an irradiation light onto the surface-to-be-measured of a sample and a photodetector which has a photosensor for detecting light reflected by the surface-to-be-measured of the sample to impinge upon the photosensor through a light receiving surface of the photodetector. The distance r between the center of the light receiving surface of the photodetector and the optical axis of the irradiation light is $r_o$, the distance h between the center of the light receiving surface and the surface-to-be-measured as measured along the optical axis of the irradiation light is $h_o$, and the angle $\theta$ which the light receiving surface forms with the surface-to-be-measured is $\theta o$, $h_o$ being the value of h at which output I of the photosensor takes a peak value on an output curve representing the change of the output I of the photosensor with the distance h when the distance h is varied under the combination of $r_o$ and $\theta o$.

9 Claims, 5 Drawing Sheets

REFLECTION DENSITY MEASURING SYSTEM

BACKGROUND OF THE INVENTION
1. Field of the Invention

This invention relates to a reflection density measuring system in which light is projected onto a surface to be measured and reflected light from the measured surface is received by a photodetector, whereby the reflection density of the surface is measured.

2. Description of the Prior Art

There has been put into practice a dry-type chemical assay slide for quantitative analysis of a particular component contained in a droplet of a sample liquid such as blood or urine. See for example Japanese Patent Publication No. 53(1978)-21677, Japanese Unexamined Patent Publication No. 55(1980)-164356.

When analyzing chemical components in a sample liquid using such a chemical assay slide, a droplet of the sample liquid is deposited on the slide and is held at a constant temperature for a predetermined time in an incubator to permit a coloring reaction, and the optical density of the color formed by the coloring reaction is optically measured. That is, measuring light containing a wavelength selected in advance according to the combination of the component to be measured in he sample liquid and the reagent contained in the reagent layer of the slide is projected onto the chemical assay slide and the optical density of the reflected light is measured. Then the content of the component to be measured is quantified on the basis of the optical density of the reflected light by colorimetry.

The optical density of the reflected light is measured by a reflection density measuring system. In the reflection density measuring system, a sample or a chemical assay slide is mounted on the system, light is projected onto a surface of the slide to be measured and reflected light from the surface to be measured is received by a photodetector.

In such a reflection density measuring system, there has been a problem that the position of the measured surface of the sample can fluctuate in the direction perpendicular to the measured surface due to fluctuation in the positioning accuracy or the dimensional accuracy of the slide, deflection of the slide, and the like. When the position of the measured surface fluctuates in the direction perpendicular thereto, the relative position between the measured surface and the photodetector varies to change the result of the measurement.

SUMMARY OF THE INVENTION

In view of the foregoing, the primary object of the present invention is to provide a reflection density measuring system in which the result of the measurement is less affected by fluctuation in the position of the measured surface perpendicular to the measured surface.

In accordance with one aspect of the present invention, there is provided a reflection density measuring system comprising a means for projecting irradiation light onto the surface-to-be-measured of a sample and a photodetector which has a photosensor for detecting light reflected by the surface-to-be-measured of the sample to impinge upon the photosensor through a light inlet side element of the photodetector, characterized in that the distance r between the center of the light inlet side element of the photodetector and the optical axis of the irradiation light is $r_o$, the distance h between the center of the light inlet side element and the surface-to-be-measured as measured along the optical axis of the irradiation light is $h_o$, and the angle $\theta$ which the light inlet side element forms with the surface-to-be-measured is $\theta_o$, $h_o$ being the value of h at which output I of the photosensor takes a peak value on an output curve representing the change of the output I of the photosensor with the distance h when the distance h is varied under the combination of $r_o$ and $\theta o$.

When the angle $\theta$ and the distance r are suitably selected, the output curve representing the relation between the distance h and the output I of the photosensor is generally an arch-like curve and the output I of the photosensor takes a peak value at a predetermined value of the distance h. The values $r_o$ and $\theta o$ are selected so that the output curve becomes an arch-like curve and the value $h_o$ is selected to be the value corresponding to a peak value of the output I of the photosensor. Near the peak, the output of the photosensor exhibits substantially no change with change in the distance h. The value of $h_o$ need not be strictly equal to the value corresponding to the peak value but may be substantially equal to the same.

In accordance with another aspect of the present invention, there is provided a reflection density measuring system comprising a means for projecting irradiation light onto the surface-to-be-measured of a sample and at least first and second photodetectors each of which has a photosensor for detecting light reflected by the surface-to-be-measured of the sample to impinge upon the photosensor through a light inlet side element of the photodetector, characterized in that when the distances h between the center of the light inlet side element of the first photodetector and a regular position of the surface-to-be-measured of the sample and between the center of the light inlet side element of the second photodetector and the regular position as measured along the optical axis of the irradiation light are respectively represented by $h_1$ and $h_2$, the angles $\theta$ which the light inlet side elements of the first and second photodetector respectively form with the surface-to-be-measured are respectively represented by $\theta 1$ and $\theta 2$, and the distrances r between the center of the light inlet side element of the first photodetector and the optical axis of the irradiation light and between the center of the light inlet side element of the second photodetector and the optical axis are respectively represented by $r_1$ and $r_2$, the first photodetector is disposed so that $h_1$ is smaller than value $h_{10}$ which is the value of h at which output $I_1$ of the photosensor of the first photodetector takes a peak value on an output curve representing the change of the output $I_1$ with the distance h when the distance h is varied under the combination of $r_1$ and $\theta_1$, and the second photodetector is disposed so that $h_2$ is larger than value $h_{20}$ which is the value of h at which output $I_2$ of the photosensor of the second photodetector takes a peak value on an output curve representing the change of the output $I_2$ with the distance h when h distance h is varied under the combination of $r_2$ and $\theta_2$, the reflection density of the surface-to-be-measured being determined on the basis of the sum of the outputs of the photosensors or on the basis of the highest of the outputs of the photosensors.

In accordance with the present invention, the photodetector may solely consist of a photosensor or may comprise a photosensor and a lens or an optical stop disposed in front of the photosensor. The term "the light inlet side element" denotes the photosensor itself

DESCRIPTION OF THE PREFERRED EMBODIMENTS

Figure 1:
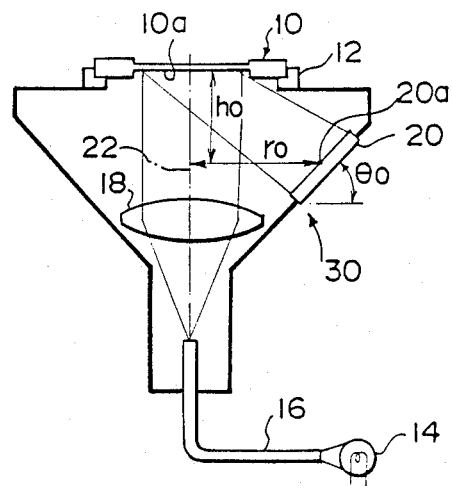
FIG. 1 is a schematic view for illustrating a reflection density measuring system in accordance with an embodiment of the present invention.

In FIG. 1, a reflection density measuring system in accordance with an embodiment of the present invention comprises a sample holder 12 for holding a sample 10, a light source 14 for emitting irradiation light, fiber optics 16 for guiding the irradiation light to impinge upon a surface-to-be-measured 10a of the sample 10 at a direction perpendicular thereto, a condenser lens 18 for condensing the irradiation light emanating from the fiber optics 16, and a photodetector 30 which has a photosensor 20 such as a silicon photodiode and receives reflection light from the surface-to-be-measured 10a.

The fiber optics 16, the condenser lens 18, the sample holder 12 and the photosensor 20 are arranged so that when a sample of a regular size is held by the sample holder 12 in a regular position, the distance h between the center 20a of the photosensor 20 and the surface-to-be-measured 10a of the sample 10 as measured along the optical axis 22 of the irradiation light is ho, the angle $\theta$ which the photosensor 20 forms with the surface-to-be-measured 10a is $\theta$o, and the distance r between the center 20a of the photosensor 20 and the optical axis 22 of the irradiation light is ro, and so that $h_o$ is the value of h at which output I of the photosensor 20 takes a peak value on an output curve representing the change of the output I of the photosensor 20 with the distance h when the distance h is varied under the combination of ro and $\theta$o.

That is, in the optical system shown in FIG. 1, when the angle $\theta$ and the distance r are suitably selected, the output curve representing the relation between the distance h and the output I of the photosensor 20 is generally an arch-like curve and the output I of the photosensor 20 takes a peak value at a predetermined value of the distance h. The values ro and $\theta$o are selected so that the output curve becomes an arch-like curve and the value ho is selected to be the value corresponding to a peak value of the output I of the photosensor 20.

Figure 2:
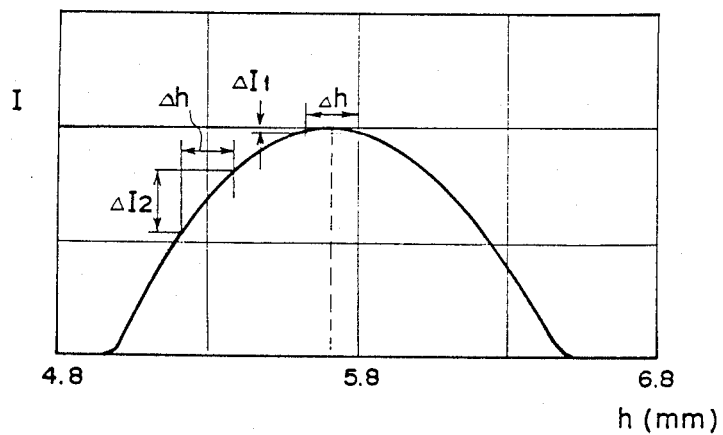
FIG. 2 is a view for illustrating the principle of operation of the embodiment shown in FIG. 1, FIGS. 3 and 4 are views similar to FIG. 1 but showing modifications of the system shown in FIG. 1.

An example of the arch-like output curve is shown in FIG. 2. The output curve shown in FIG. 2 represents the change of the output I of the photosensor 20 with the distance h when the distance h is varied from about 5.0 mm to about 6.5 mm with ro being 8.75 mm and $\theta$o being 45°. As can be seen from FIG. 2, the output I takes a peak value when the distance h is about 5.7 mm in this case.

Since the value ho is selected to be the value of the distance h corresponding to the peak value of the output I of the photosensor 20, a change of the actual distance h between the surface-to-be-detected 10a and the center 20a of the photosensor 20 as measured along the optical axis 22 near the value ho which can occur due to fluctuation in the positioning accuracy or the dimensional accuracy of the slide, deflection of the slide, and the like can fluctuate the output I of the photosensor only by a slight value indicated at $\Delta I_1$. The value $\Delta I_1$ is much smaller than the value of $\Delta I_2$ which is the fluctuation of the output I when the distance h is varied for the same value from a value which is not corresponding to the peak value of the output I.

Though in the embodiment described above, the values ro and $\theta$o are selected so that the output curve becomes an arch-like curve, the values may be selected to provide an output curve of a different shape so long as the curve has a peak value or an inflection point.

Figure 3:
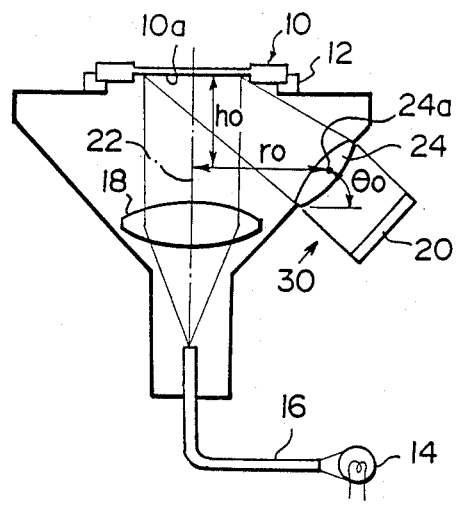
Figure 4:
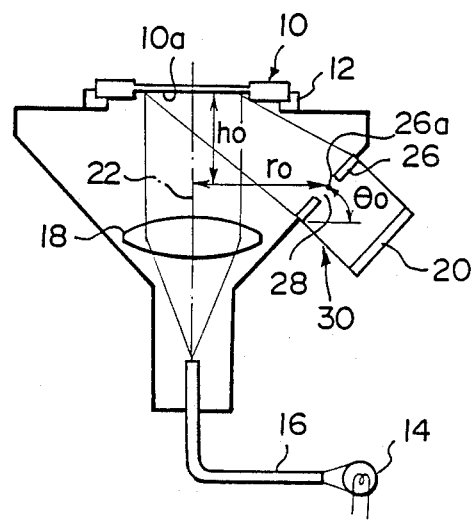

FIGS. 3 and 4 show modifications of the optical system shown in FIG. 1. In the figures, the parts analogous to the parts shown in FIG. 1 are given the same reference numerals and are not further described. In the modifications shown in FIG. 3, the photodetector 30 comprises a photosensor 20 and a lens 24 disposed in front of the photosensor 20. In this modification, the fiber optics 16, the condenser lens 18, the sample holder 12 and the photodetector 30 are arranged so that when a sample of a regular size is held by the sample holder 12 in a regular position, the distance h between the center 24a of the lens 24 and the surface-to-be-measured 10a of the sample 10 as measured along the optical axis 22 of the irradiation light is ho, the angle $\theta$ which the lens 24 forms with the surface-to-be-measured 10a is $\theta$o, and the distance r between the center 24a of the lens 24 and the optical axis 22 of the irradiation light is ro, so that ho is the value of h at which output I of the photosensor 20 takes a peak value on an output curve representing the change of the output I of the photosensor 20 with the distance h when the distance h is varied under the combination of ro and $\theta$o.

In the modification shown in FIG. 4, the photodetector 30 comprises a photosensor 20 and an optical stop 26 having an aperture 28 disposed in front of the photosensor 20. In this modification, the fiber optics 16, the condenser lens 18, the sample holder 12 and the photodetector 30 are arranged so that when a sample of the regular size is held by the sample holder 12 in the regular position, the distance h between the center 26a of the stop 26 (the center 28a of the aperture 28) and the surface-to-be-measured 10a of the sample 10 as measured along the optical axis 22 of the irradiation light is ho, the angle $\theta$ which the stop 26 forms with the surface-to-be-measured 10a is $\theta$o, and the distance r between the center 26a of the stop 26 and the optical axis 22 of the irradiation light is ro, so that ho is the value of h at which output I of the photosensor 20 takes a peak value on an output curve representing the change of the output I of the photosensor 20 with the distance h when the distance h is varied under combination of ro and θo.

Also in the modifications shown in FIGS. 3 and 4, since the value ho is selected to be the value of the distance h corresponding to the peak value of the output I of the photosensor 20, a change of the actual distance h between the surface-to-be-detected 10a and the center 24a of the lens 24 or the center 26a of the stop 26 as measured along the optical axis 22 near the value ho can fluctuate the output I of the photosensor only by a slight value. In the embodiment described above, only a single photodetector is provided. However, a plurality of photodetectors may be provided. In this case, at least one of the photodetectors should be positioned to meet the condition described above.

Figure 5:
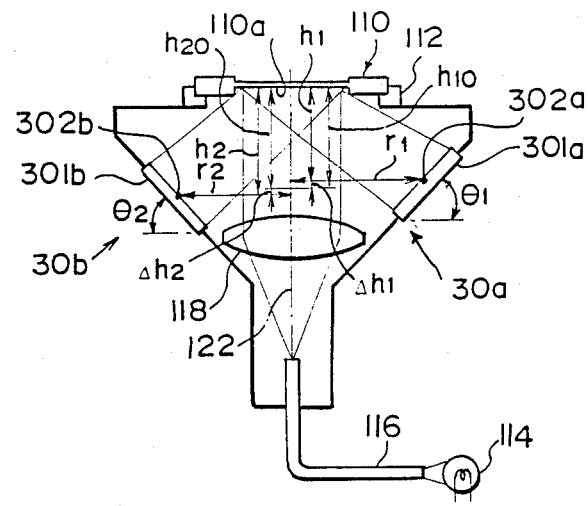
FIG. 5 is a schematic view illustrating the reflection density measuring system in accordance with another embodiment of the present invention.
Figure 6:
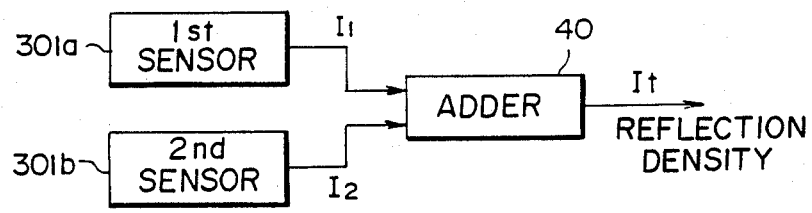
FIG. 6 is a block diagram of the circuit for determining the reflection density on the basis of the outputs of the photosensor in the embodiment.

FIGS. 5 and 6 show still another embodiment of the present invention. In FIG. 5, the system of this embodiment comprises a sample holder 112 for holding a sample 110, a light source 114 for emitting irradiation light, fiber optics 116 for guiding the irradiation light to impinge upon a surface-to-be-measured 110a of the sample 110 perpendicular thereto, a condenser lens 118 for condensing the irradiation light emanating from the fiber optics 116, and first and second of photodetectors 30a and 30b which respectively have photosensors 301a and 301b such as silicon photodiodes and receive reflection light from the surface-to-be-measured 110a.

The fiber optics 116, the condenser lens 118, the sample holder 112 and the photosensors 301a and 301b are arranged so that when a sample of a regular size is held by the sample holder 112 in a regular position, the distances h between the center 302a of the first photosensor 301a and a regular position of the surface-to-be-measured 110a of the sample 110 and between the center 302b of the second photosensor 301b and the regular position as measured along the optical axis 122 of the irradiation light are respectively $h_1$ and $h_2$, the angles $\theta$ which the photosensors 301 and 301b respectively form with the surface-to-be-measured 110a are $\theta_1$ and $\theta_2$, and the distances r between the center 302a of the first photosensor 301a and the optical axis 122 of the irradiation light and between the center 302b of the second photosensor 301b and the optical axis 122 are respectively $r_1$ and $r_2$ so that $h_1$ is smaller by $\Delta h_1$ than value $h_{10}$ which is the value of h at which output $I_1$ of the first photosensor 301a takes a peak value on an output curve representing the change of the output $I_1$ with the distance h when the distance h is varied under the combination of $r_1$ and $\theta_1$, and $h_2$ is larger by $\Delta h_2$ than value $h_{20}$ which is the value of h at which output $I_2$ of the second photosensor 301b takes a peak value on an output curve representing the change of the output $I_2$ with the distance h when the distance h is varied under the combination of $r_2$ and $\theta_2$.

That is, in the optical system shown in FIG. 5, when the angle $\theta$ and the distance r are suitably selected, the output curve representing the relation between the distance h and the output I of the photosensor is generally an arch-like curve and the output I of the photosensor takes a peak value at a predetermined value of the distance h. The values $r_1$ and $\theta_1$, and values $r_2$ and $\theta_2$ are selected so that the output curves of the corresponding photosensors become arch-like curves and the value $h_1$ is selected to be smaller by $\Delta h_1$ than the value $h_{10}$ which is the value of h at which the output $I_1$ of the first photosensor 301a takes a peak value on the arch-like output curve representing the change of the output $I_1$ and $h_2$ is selected to be larger by $\Delta h_2$ than the value $h_{20}$ which is the value of h at which the output $I_2$ of the second photosensor 301b takes a peak value on the arch-like output curve representing the change of the output $I_2$.

In this embodiment, the first and second photosensors 301a and 301b are connected to an adder 140 as shown in FIG. 6, and the outputs $I_1$ and $I_2$ of the first and second photosensors 301a and 301b are added together by the adder 140. The reflection density of the sample 110 is determined on the basis of the output of the adder 140 or the sum $I_t$ of the outputs $I_1$ and $I_2$.

Figure 7:
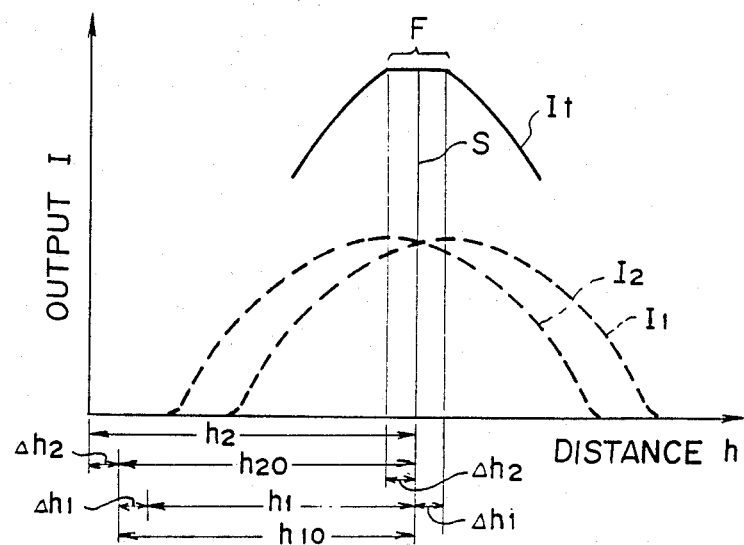
FIG. 7 is a view for illustrating the principle of operation of the embodiment.

FIG. 7 shows the relations between the distance h and the output $I_1$, between the distance h and the output $I_2$, and between the distance h and the sum $I_t$ of the outputs $I_1$ and $I_2$. Since the first and second photosensors 301a and 301b are disposed as described above, the output $I_1$ of the first photosensor 301a takes the peak value when the surface-to-be-measured 110a is positioned higher than the regular position S of the surface-to-be-measured 110a of the sample 110 by $\Delta h_1$ and the output $I_2$ of the second photosensor 301b takes the peak value when the surface-to-be-measured 110a is positioned lower than the regular position S (on a sample of the regular size held by the sample holder 112 in the regular position) by $\Delta h_2$ as can be understood from FIG. 7. Accordingly, the sum $I_t$ of the outputs $I_1$ and $I_2$, i.e., the output of the adder 140 has a substantially flat peak F extending on opposite sides of the value of h corresponding to the regular position S in lengths respectively corresponding to the values of $\Delta h_1$ and $\Delta h_2$. Therefore, in accordance with this embodiment, the output $I_t$ of the adder 140 exhibits substantially no change even if the position of the surface-to-be-measured 110a fluctuates along the optical axis 122 of the irradiation light so long as the surface-to-be-measured 110a is positioned in width, and accordingly positioning accuracy of the sample 110 less affects measuring accuracy of optical density of the sample 110. It is preferred, though not necessary, that $\Delta h_1$ and $\Delta h_2$ are equal to each other in value.

Figure 8:
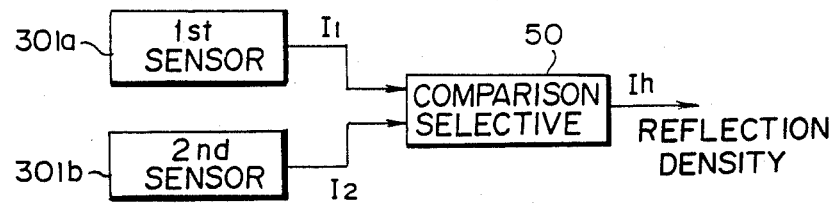
FIG. 8 is a view similar to FIG. 6 but showing the circuit for determining the reflection density on the basis of the outputs of the photosensors in still anothe embodiment of the present invention.

Still another embodiment of the present invention will now be described with reference to FIGS. 8 and 9. The optical density measuring system of this embodiment has an optical system identical to the optical system shown in FIG. 5 and differs from the preceding embodiment in that the photosensors 301a and 310b are connected to a comparison selective output circuit 150 instead of the adder 140. The comparison selective output circuit 150 compares the outputs of the photosensors 301a and 301b and outputs the higher of them ($I_h$). The reflection density of the sample 110 is determined on the basis of the output of the comparison selective output circuit 150 or the higher one of the outputs of the photosensors 301a and 301b of the first and second photodetectors 30a and 30b.

Figure 9:
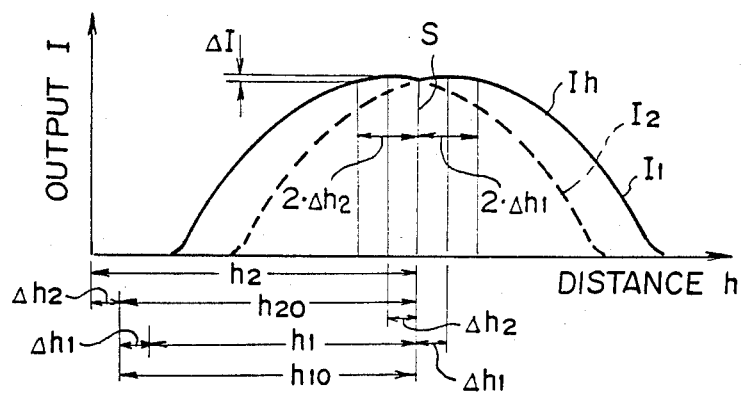
FIG. 9 is a view for illustrating the principle of operation of the embodiment.

FIG. 9 shows the relations between the distance h and the output $I_1$, between the distance h and the output $I_2$, and between the distance h and the output $I_h$ of the comparison selective output circuit 150. The output curves of the outputs $I_1$ and $I_2$ are as described above in conjunction with the preceding embodiment and accordingly the output curve of the output $I_h$ has two peaks on opposite sides of the value of h corresponding to the regular position S of the surface-to-be-measured 110a of the sample positioned in the regular position as shown by the solid line in FIG. 9, the peaks respectively corresponding to the peaks of the output curves of the outputs $I_1$ and $I_2$.

As described above in conjunction with the embodiment shown in FIG. 1, the output of the photosensor exhibits only a slight change with change in the distance h near a peak of the output curve and accordingly by measuring the reflection density near the peak of the output curve, the reflection density can be precisely measured even if the sample 110 is displaced from the regular position within a certain range. For example, assuming that the reflection density is measured on the basis of only the output $I_2$ of the second photosensor 301b as in the embodiment shown in FIG. 1, the sample 110 may be displaced from the regular position by $\Delta h_2$ on opposite sides of the peak. That is, in this case, the vertical (along the optical axis of the irradiation light) displacement of the sample 110 from the regular position within $\Delta h_2$ on each side of the regular position can be allowed. That is, the allowable range of the vertical displacement of the sample 110 is $2 \cdot \Delta h_2$. On the other hand, in the case of this embodiment in which the reflection density is determined on the basis of the higher of the outputs $I_1$ and $I_2$ of the first and second photosensors 301a and 301b, the allowable range of the vertical displacement of the sample 110 is further widened to $2 \cdot \Delta h_1 + 2 \cdot \Delta h_2$ as can be understood from FIG. 9. Also in this embodiment, it is preferred, though not necessary, that $\Delta h_1$ and $\Delta h_2$ be equal to each other.

Though in the two embodiments described with reference to FIGS. 5 to 9, the values $r_1$ and $\theta_1$, or the values $r_2$ and $\theta_2$ are selected so that the output curve becomes an arch-like curve, the values may be selected to provide an output curve of a different shape so long as the curve has a peak value or an inflection point.

Figure 10:
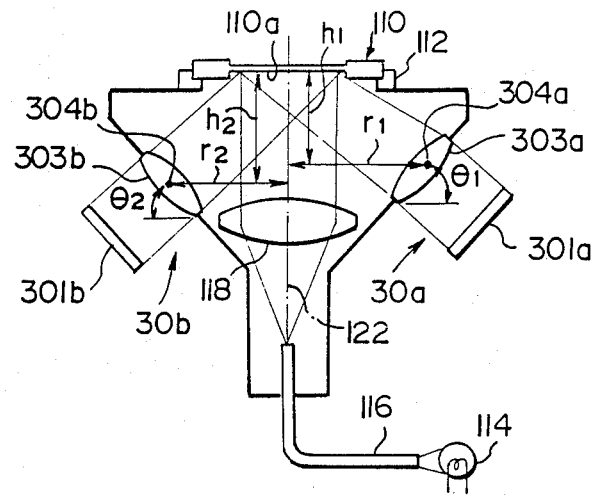
FIGS. 10 and 11 are views similar to FIG. 5 but showing modifications of the system shown in FIG. 5.
Figure 11:
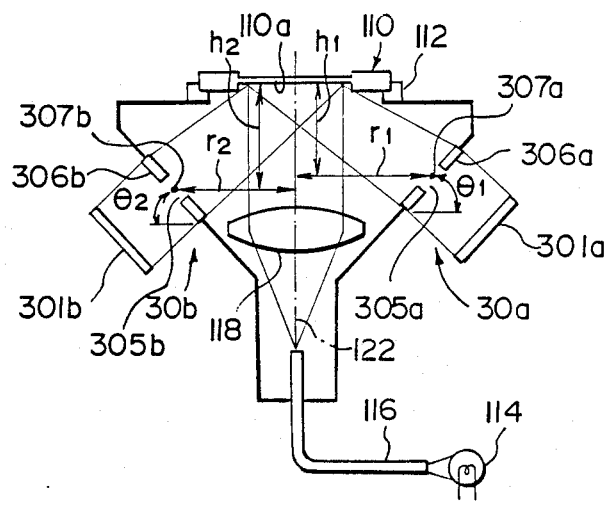

FIGS. 10 and 11 show modifications of the optical system shown in FIG. 5.

In the modification shown in FIG. 10, the first and second photodetectors 30a and 30b comprise photosensors 301a and 301b and lenses 303a and 303b disposed in front of the photosensors 301a and 301b. The fiber optics 116, the condenser lens 118, the sample holder 112 and the photodetectors 30a and 30b are arranged so that when a sample of the regular size is held by the sample holder 112 in the regular position, the distances h between the center 304a of the lens 303a and a regular position of the surface-to-be-measured 110a of the sample 110 and between the center 304b of the lens 303b and the regular position as measured along the optical axis 122 of the irradiation light are respectively $h_1$ and $h_2$, the angles $\theta$ which the lenses 303a and 303b respectively form with the surface-to-be-measured 110a are $\theta_1$ and $\theta_2$, and the distances r between the center 304a of the lens 303a and the optical axis 122 of the irradiation light and between the center 304b of the lens 303b and the optical axis 122 are respectively $r_1$ and $r_2$ and so that $h_1$ is smaller by $\Delta h_1$ than value $h_{10}$ which is the value of h at which output $I_1$ of the first photosensor 301a takes a peak value on an output curve representing the change of the output $I_1$ with the distance h when the distance h is varied under the combination of $r_1$ and $\theta_1$, and $h_2$ is larger by $\Delta h_2$ than value $h_{20}$ which is the value of h at which output $I_2$ of the second photosensor 301b takes a peak value on an output curve representing the change of the output $I_2$ with the distance h when the distance h is varied under the combination of $r_2$ and $\theta_2$.

In the modification shown in FIG. 11, the first and second photodetectors 30a and 30b comprise photosensors 301a and 301b and optical stops 303a and 306b respectively having apertures 305a and 305b disposed in front of the photosensors 301a and 301b. The fiber optics 116, the condenser lens 118, the sample holder 112 and the photodetectors 30a and 30b are arranged so that when a sample of the regular size is held by the sample holder 112 in the regular position, the distances h between the center 307a of the aperture 305a (the stop 306a) and a regular position of the surface-to-be-measured 110a of the sample 110 and between the center 307b of the aperture 305b (the stop 306b) and the regular position as measured along the optical axis 122 of the irradiation light are respectively $h_1$ and $h_2$, the angles $\theta$ which the stops 306a and 306b respectively form with the surface-to-be-measured 110a are $\theta_1$ and $\theta_2$, and the distances r between the center 307a of the aperture 307a and the optical axis 122 of the irradiation light and between the center 307b of the aperture 307b and the optical axis 122 are respectively $r_1$ and $r_2$ so that $h_1$ is smaller by $\Delta h_1$ than value $h_{10}$ which is the value of h at which output $I_1$ of the first photosensor 301a takes a peak value on an output curve representing the change of the output $I_1$ with the distance h when the distance h is varied under the combination of $r_1$ and $\theta_1$, and $h_2$ is larger by $\Delta h_2$ than value $h_{20}$ which is the value of h at which output $I_2$ of the second photosensor 301b takes a peak value on an output curve representing the change of the output $I_2$ with the distance h when the distance h is varied under the combination of $r_2$ and $\theta_2$.

The optical systems shown in FIGS. 10 and 11 may be associated with either of the circuits shown in FIGS. 6 and 8 to obtain the same results as one of the embodiments described above in conjunction with FIGS. 5 to 9.

Though in the embodiments shown in FIGS. 5 to 9, a pair of photodetectors are provided, three or more photodetectors may be used. In this case, at least two of the photodetectors should be positioned to meet the condition described above. Further, it is preferred, that the third photodetector be disposed so that its output takes a peak value at the value of h corresponding to the regular position of the surface-to-be-measured 110a.

I claim:

1. A reflection density measuring system comprising a means for projecting an irradiation light onto the surface-to-be-measured of a sample and at least first and second of photodetectors each of which has a photosensor for detecting light reflected by the surface-to-be-measured of the sample to impinge upon the photosensor through a light inlet side element of the photodetector, characterized in that when the distances h between the center of the light inlet side element of the first photodetector and a regular position of the surface-to-be-measured of the sample and between the center of the light inlet side element of the second photodetector and the regular position as measured along the optical axis of the irradiation light are respectively represented by $h_1$ and $h_2$, the angles $\theta$ which the light inlet side elements of the first and second photodetector respectively form with the surface-to-be-measured are respectively represented by $\theta 1$ and $\theta 2$, and the distances r between the center of the light inlet side element of the first photodetector and the optical axis of the irradiation light and between the center of the light inlet side element of the second photodetector and the optical axis are respectively represented by $r_1$ and $r_2$, the first photodetector is disposed so that $h_1$ is smaller than value $h_{10}$ which is the value of h at which output $I_1$ of the photosensor of the first photodetector takes a peak value on an output curve representing the change of the output $I_1$ with the distance h when the distance h is varied under the combination of $r_1$ and $\theta_1$, and the second photodetector is disposed so that $h_2$ is larger than value $h_{20}$ which is the value of h at which output $I_2$ of the photosensor of the second photodetector takes a peak value on an output curve representing the change of the output $I_2$ with the distance h when the distance h is varied under the combination of $r_2$ and $\theta_2$, the reflection density of the surface-to-be-measured being determined on the basis of the sum of the outputs of the photosensors.

2. A reflection density measuring system as defined in claim 1 in which each of said photodetectors solely consists of a photosensor and said light inlet side element is the photosensor itself.

3. A reflection density measuring system as defined in claim 1 in which each of said photodetectors comprises a photosensor and a lens disposed in front of the photosensor and said light inlet side element is the lens.

4. A reflection density measuring system as defined in claim 1 in which each of said photodetector comprises a photosensor and an optical stop disposed in front of the photosensor and said light inlet side element is the optical stop.

5. A reflection density measuring system comprising a means for projecting an irradiation light onto the surface-to-be-measured of a sample and at least first and second photodetectors each of which has a photosensor for detecting light reflected by the surface-to-be-measured of the sample to impinge upon the photosensor through a light inlet side element of the photodetector, characterized in that when the distances h between the center of the light inlet side element of the first photodetector and a regular position of the surface-to-be-measured of the sample and between the center of the light inlet side element of the second photodetector and the regular position as measured along the optical axis of the irradiation light are respectively represented by $h_1$ and $h_2$, the angles $\theta$ which the light inlet side elements of the first and second photodetector respectively form with the surface-to-be-measured are respectively represented by $\theta_1$ and $\theta_2$, and the distances r between the center of the light inlet side element of the first photodetector and the optical axis of the irradiation light and between the center of the light inlet side element of the second photodetector and the optical axis are respectively represented by $r_1$ and $r_2$, the first photodetector is disposed so that $h_1$ is smaller than value $h_{10}$ which is the value of h at which output $I_1$ of the photosensor of the first photodetector takes a peak value on an output curve representing the change of the output $I_1$ with the distance h when the distance h is varied under the combination of $r_1$ and $\theta_1$, and the second photodetector is disposed so that $h_2$ is larger than value $h_{20}$ which is the value of h at which output $I_2$ of the photosensor of the second photodetector takes a peak value on an output curve representing the change of the output $I_2$ with the distance h when the distance h is varied under the combination of $r_2$ and $\theta_2$, the reflection density of the surface-to-be-measured being determined on the basis of the highest of the outputs of the photosensors.

6. A reflection density measuring system as defined in claim 5 in which each of said photodetectors solely consists of a photosensor and said light inlet side element is the photosensor itself.

7. A reflection density measuring system as defined in claim 5 in which each of said photodetectors comprises a photosensor and a lens disposed in front of the photosensor and said light inlet side element is the lens.

8. A reflection density measuring system as defined in claim 5 in which each of said photodetector comprises a photosensor and an optical stop disposed in front of the photosensor and said light inlet side element is the optical stop.

9. A reflection density measuring system comprising means for projecting an irradiation light onto a surface-to-be-measured of a sample at at least first and second photodetectors each of which as a photosensor for detecting light reflected by the surface-to-be-measured of the sample to impinge upon the photosensor through a light inlet side element of the photodetector, characterized in that when the distances h between the center of the light inlet side element of the first photodetector and a regular position of the surface-to-be-measured of the sample and between the center of the light inlet side element of the second photodetector and the regular position as measured along the optical axis of the irradiation light are respectively represented by $h_1$ and $h_2$, the angles $\theta$ which the light inlet side elements of the first and second photodetector respectively form with the surface-to-be-measured are respectively represented by $\theta 1$ and $\theta 2$, and the distances r between the center of the light inlet side element of the second photodetector and the optical axis are respectively represented by $r_1$ and $r_2$, the first photodetector is disposed so that $h_1$ is smaller than a value $h_{10}$ which is the value of h at which output $I_1$ of the photosensor of the first photodetector takes a peak value on an output curve representing the change of the output $I_1$ with the distance h when the distance h is varied under the combination of $r_1$ and $\theta 1$, and the second photodetector is disposed so that $h_2$ is larger than value $h_{20}$ which is the value of h at which output $h_2$ is larger than value $h_{20}$ which is the value of h at which output $I_2$ of the photosensor of the second photodector takes a peak value on an output curve representing the change of the output $I_2$ with the distance h when the distance h is varied under the combination of $r_2$ and $\theta 2$, the reflection density of the surface-to-be-measured being determined on the basis of a combination of the outputs of the photosensors.

* * * * *